United States Patent
Krager et al.

(10) Patent No.: US 12,064,113 B2
(45) Date of Patent: Aug. 20, 2024

(54) ANTI-BUCKLING ACTUATION MEMBERS FOR A SURGICAL INSTRUMENT

(71) Applicant: BOLDER SURGICAL, LLC, Louisville, CA (US)

(72) Inventors: Perry Krager, Colorado Springs, CO (US); Erin McConnaghy, Colorado Springs, CO (US); Allison Lyle, Boulder, CO (US); Nathan Steketee, Westminster, CO (US)

(73) Assignee: Bolder Surgical, LLC, Louisville, CO (US)

( * ) Notice: Subject to any disclaimer, the term of this patent is extended or adjusted under 35 U.S.C. 154(b) by 0 days.

(21) Appl. No.: 18/139,805

(22) Filed: Apr. 26, 2023

(65) Prior Publication Data
US 2023/0263524 A1    Aug. 24, 2023

Related U.S. Application Data

(63) Continuation of application No. 17/246,873, filed on May 3, 2021, now Pat. No. 11,653,921.

(60) Provisional application No. 63/019,470, filed on May 4, 2020.

(51) Int. Cl.
*A61B 17/072* (2006.01)
*A61B 17/29* (2006.01)

(52) U.S. Cl.
CPC .............. *A61B 17/07207* (2013.01); *A61B 2017/07257* (2013.01); *A61B 2017/07271* (2013.01); *A61B 2017/07285* (2013.01); *A61B 2017/2902* (2013.01); *A61B 2017/2933* (2013.01)

(58) Field of Classification Search
CPC ............ A61B 17/072; A61B 17/07207; A61B 2017/07285; A61B 2017/2927; A61B 2017/00398; A61B 2017/0046
USPC ...................................................... 227/180.1
See application file for complete search history.

(56) References Cited

U.S. PATENT DOCUMENTS

| 3,079,606 A | 3/1963 | Bobrov |
| 3,490,675 A | 1/1970 | Green |
| 3,499,571 A | 3/1970 | Green |
| 4,576,167 A | 3/1986 | Noiles |

(Continued)

FOREIGN PATENT DOCUMENTS

| EP | 1604607 | 12/2005 |
| JP | 2002-165801 | 6/2002 |

(Continued)

OTHER PUBLICATIONS

Non-Final Office Action for U.S. Appl. No. 17/246,873 dated Oct. 4, 2022.

(Continued)

*Primary Examiner* — Jacob A Smith
(74) *Attorney, Agent, or Firm* — Vista IP Law Group, LLP

(57) ABSTRACT

An endoscopic surgical instrument has a distal end configured to perform an action on tissue; a proximal end; a beam; a drive rod; and at least one rail supporting at least one bearing, the at least one bearing movable relative to the at least one rail. The distal end of the instrument is configured to receive at least a portion of the beam, the beam movable longitudinally in response to an action on the drive rod. The at least one rail is shaped and configured to contact the beam tangentially to prevent the beam from buckling as the beam is moved longitudinally.

23 Claims, 6 Drawing Sheets

(56) References Cited

U.S. PATENT DOCUMENTS

| | | |
|---|---|---|
| 5,040,715 A | 8/1991 | Green |
| 5,240,163 A | 8/1993 | Stein et al. |
| 5,307,976 A | 5/1994 | Olson |
| 5,312,023 A | 5/1994 | Green |
| 5,318,221 A | 6/1994 | Green |
| 5,326,013 A | 7/1994 | Green |
| 5,332,142 A | 7/1994 | Robinson |
| 5,462,546 A | 10/1995 | Rydell |
| 5,673,841 A | 10/1997 | Schulze |
| 5,865,361 A | 2/1999 | Milliman et al. |
| 6,763,993 B2 | 7/2004 | Bolduc et al. |
| RE38,708 E | 3/2005 | Bolanos et al. |
| 7,637,409 B2 | 12/2009 | Marczyk |
| 7,841,502 B2 | 11/2010 | Walberg et al. |
| 7,950,560 B2 | 5/2011 | Zemlok et al. |
| 8,006,886 B2 | 8/2011 | Sonnenschein et al. |
| 9,539,021 B2 | 1/2017 | Mata et al. |
| 9,750,497 B2 | 9/2017 | Mata et al. |
| 10,569,052 B2 | 2/2020 | Kokish et al. |
| 2004/0232201 A1 | 11/2004 | Wenchell et al. |
| 2005/0023324 A1 | 2/2005 | Doll et al. |
| 2005/0203507 A1 | 9/2005 | Truckai et al. |
| 2006/0025811 A1 | 2/2006 | Shelton, IV |
| 2010/0193567 A1 | 8/2010 | Scheib et al. |
| 2011/0290851 A1 | 12/2011 | Shelton, IV |
| 2012/0080332 A1 | 4/2012 | Shelton, IV et al. |
| 2013/0008937 A1 | 1/2013 | Viola |
| 2015/0005805 A1* | 1/2015 | Kesten ............ A61F 5/08 606/196 |
| 2016/0367256 A1* | 12/2016 | Hensel ............ A61B 17/105 |
| 2017/0007236 A1 | 1/2017 | Shelton, IV et al. |
| 2017/0231633 A1 | 8/2017 | Marczyk et al. |
| 2017/0290584 A1* | 10/2017 | Jasemian ............ A61B 17/072 |
| 2018/0125485 A1 | 5/2018 | Beardsley et al. |
| 2018/0250006 A1 | 9/2018 | Bucciaglia et al. |
| 2018/0317913 A1* | 11/2018 | Beardsley ........ A61B 17/07207 |

FOREIGN PATENT DOCUMENTS

| | | |
|---|---|---|
| JP | 2010-069304 | 4/2010 |
| WO | WO 2010/027693 | 3/2010 |
| WO | WO 2012/040981 | 4/2012 |

OTHER PUBLICATIONS

Amendment Response to NFOA for U.S. Appl. No. 17/246,873 dated Dec. 1, 2022.

Notice of Allowance for U.S. Appl. No. 17/246,873 dated Jan. 6, 2023.

Assion, Jean-Charles, Extended European Search Report for European Application No. 13870240.2, Jan. 19, 2017, 18 pages, European Patent Office, Munich, Germany.

Assion, Jean Charles, Supplementary Partial European Search Report, re European Application No. 13870240.2 Dec. 8, 2016, 11 pages, EPO, Munich, Germany.

Inone, Tetsuo, Office Action (translation thereof) re Japanese Patent Application No. 2015-551727, Nov. 1, 2016, 3 pages, JPO, Japan.

Krynski, William, International Search Report and Written Opinion re PCT Application No. PCT/US2013/077801, Mar. 3, 2014, 8 pages, USPTO, Alexandria, Virginia.

Lopez, Michelle, Office Action re U.S. Appl. No. 13/952,630, Apr. 18, 2016, 24 pages, USPTO, Alexandria, Virginia.

Lopez, Michelle, Office Action re U.S. Appl. No. 14/275,753, Nov. 9, 2016, 18 pages, USPTO, Alexandria, Virginia.

Moon, Kiwhan, International Preliminary Report on Patentability re: PCT Application No. PCT/US2013/077801, Jul. 7, 2015, 5 pages, WIPO, Geneva, Switzerland.

Oya, Shizuo, Office Action re Japanese Patent Application No. 2017-173942, (translation thereof), Aug. 14, 2018, 5 pages. JPO, Japan.

Schneider, Laura, Response to Office Action re U.S. Appl. No. 14/275,753, Feb. 1, 2017, 11 pages, USPTO, Alexandria, Virginia.

Schneider, Laura, Response to Office Action re U.S. Appl. No. 13/952,630, Jul. 8, 2016, 9 pages, USPTO, Alexandria, Virgina.

Yamaguchi, Kenichi, Office Action re Japanese Patent Application No. 2017-173942, (translation thereof), May 7, 2019, 6 pages, JPO, Japan.

\* cited by examiner

ANTI-BUCKLING ACTUATION MEMBERS FOR A SURGICAL INSTRUMENT

CROSS-REFERENCE TO RELATED APPLICATIONS

This application is a continuation of U.S. patent application Ser. No. 17/246,873 filed on May 3, 2021, which claims priority to U.S. Provisional Application No. 63/019,470, filed May 4, 2020 and entitled "Anti-buckling Actuation Members for a Surgical Instrument." The entireties of the above applications are expressly incorporated by reference for all proper purposes herein.

FIELD

This invention is related to surgical instruments. Specifically, but not intended to limit the invention, embodiments of the invention are related to endoscopic surgical instruments.

BACKGROUND

A number of endoscopic surgical instruments are available on the market. In many cases, it is desirable to provide surgical instruments with reduced envelope diameters, which is believed to improve surgical outcomes. Reducing the envelope diameter of surgical instruments presents, however, challenges, because one cannot simply scale down known instruments. There therefore remains a need for smaller endoscopic instruments.

SUMMARY

An endoscopic surgical instrument has a distal end configured to perform an action on tissue; a proximal end; a beam; a drive rod; and at least one rail supporting at least one bearing, the at least one bearing movable relative to the at least one rail. The distal end of the instrument is configured to receive at least a portion of the beam, the beam movable longitudinally in response to an action on the drive rod. The at least one rail is shaped and configured to contact the beam tangentially to prevent the beam from buckling as the beam is moved longitudinally.

BRIEF DESCRIPTION ON THE DRAWINGS

DETAILED DESCRIPTION

Figure 1:
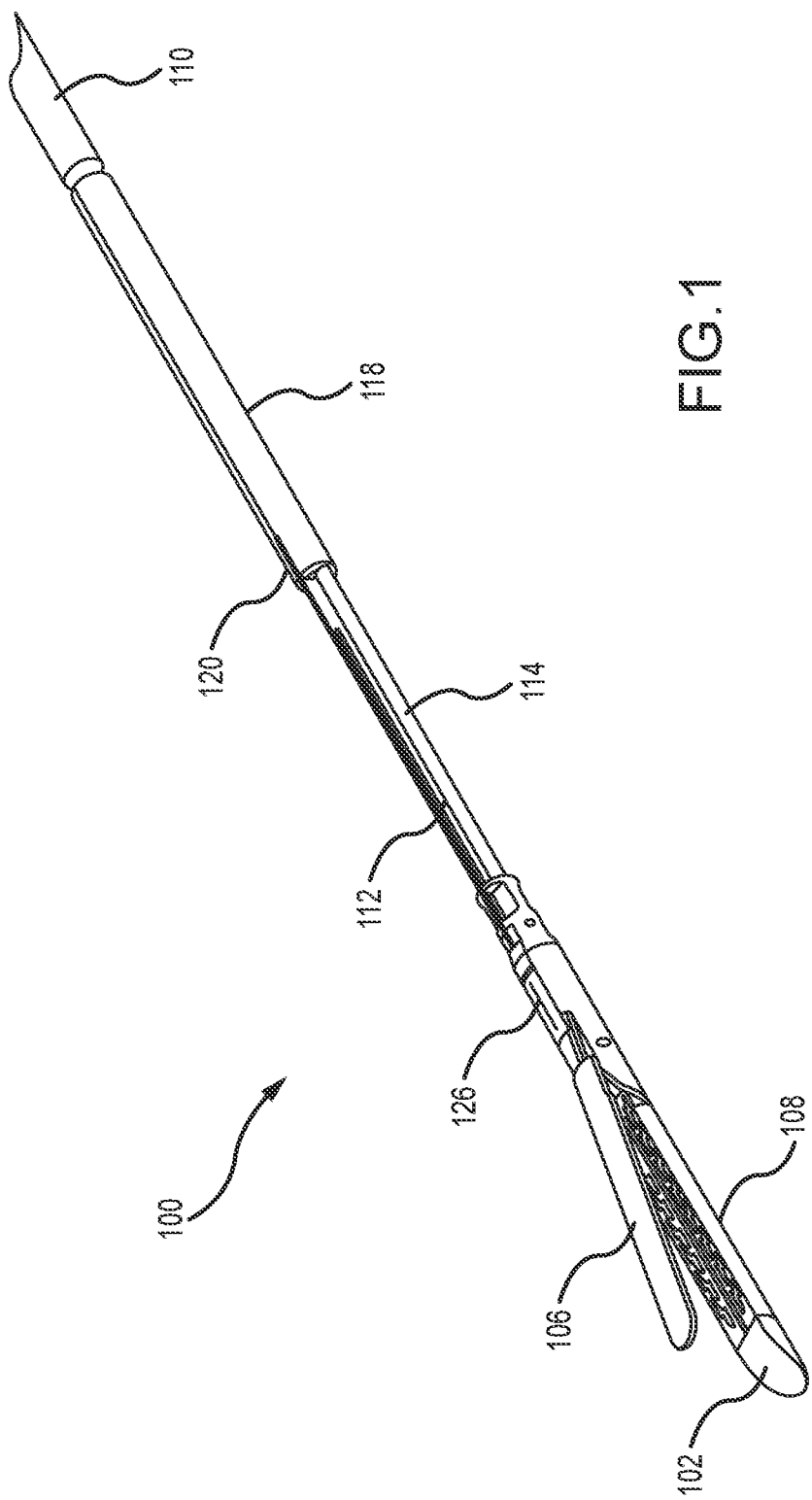
FIG. 1 is a perspective view of an exemplary laparoscopic surgical instrument without a housing for clarity.
Figure 2:
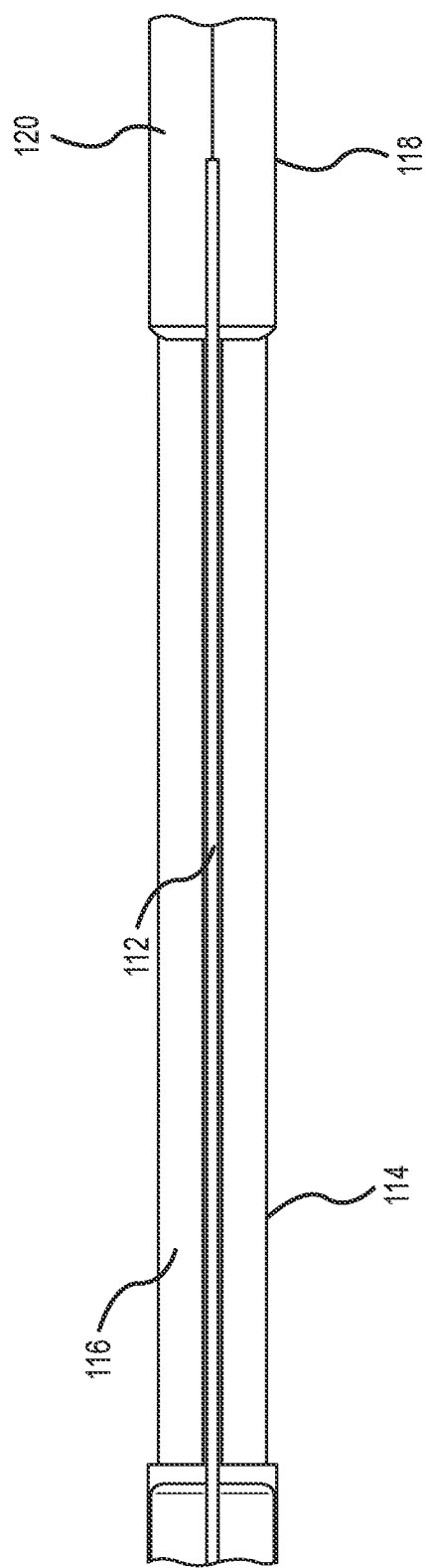
FIG. 2 is a top view of some features of the instrument.
Figure 3:
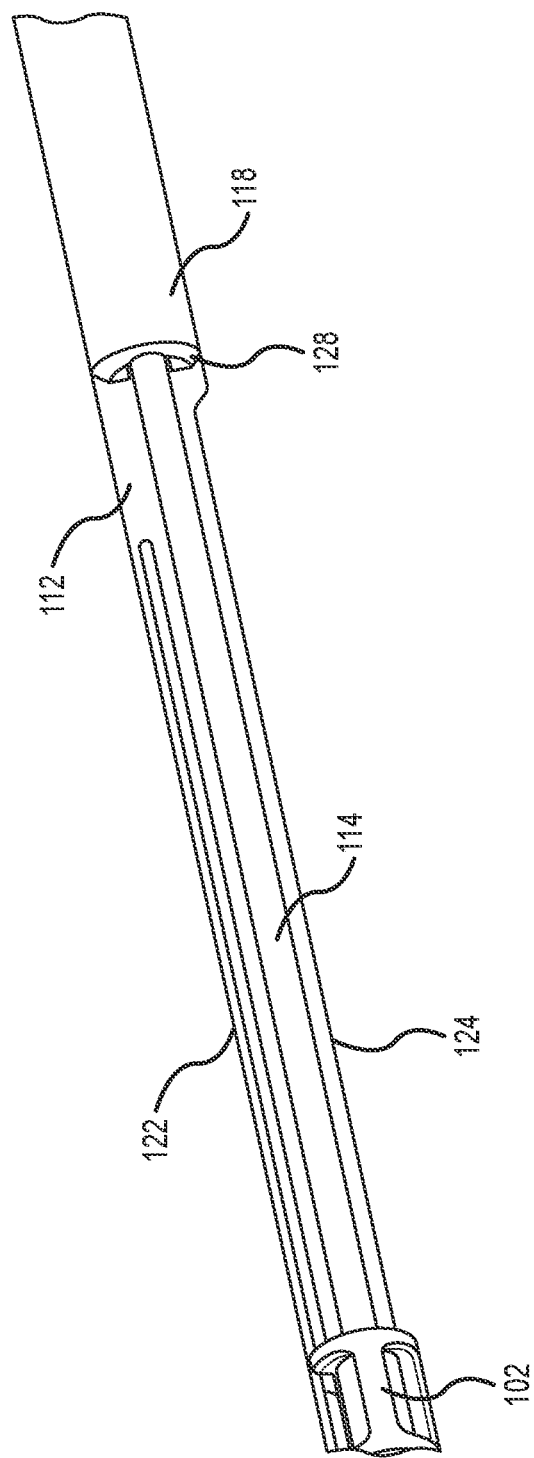
FIG. 3 is a perspective view of some features of the instrument.
Figure 4:
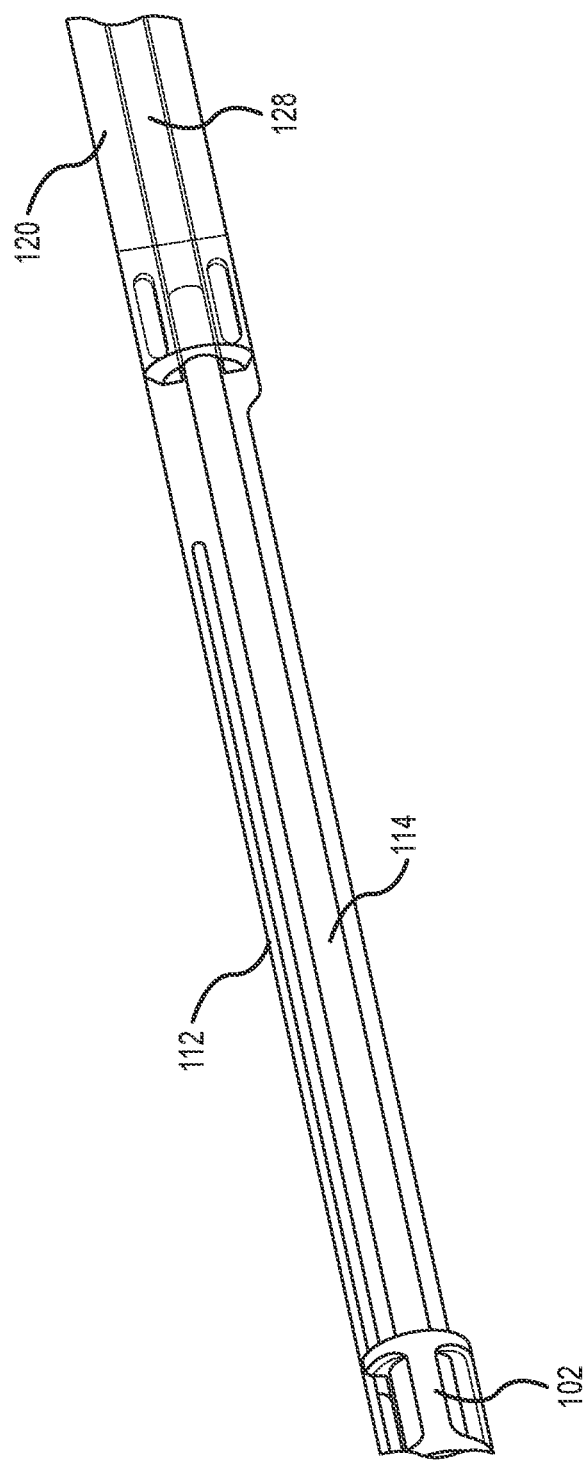
FIG. 4 is a perspective view of some features of the instrument, with some features drawn in transparent lines.

Before turning to embodiments disclosed herein, problems with known devices are described. Many surgical instruments include, for example, a distal end with jaws or an anvil and cartridge. An actuator causes the distal end to close or clamp about tissue. The same or a different actuator may deploy staples onto the clamped tissue. Another actuator may cause a cutting mechanism, usually a centrally-located knife, to sever the stapled tissue. These designs generally function as intended.

However, it is desirable to provide smaller instruments, and smaller instruments, in order to fit through a cannula or trocar, require very thin cutting mechanisms and actuators, such that actuation forces that are normally acceptable would cause the mechanisms to buckle or break. There is therefore a need for a smaller endoscopic instrument that addresses the problem of actuation forces. The Applicant solves this problem by providing an instrument 100 that reduces the necessary actuation forces and/or supports the actuation mechanism, the details of which are described herein.

With reference now to FIGS. 1-4, an exemplary endoscopic surgical instrument 100 is shown without a housing and described in detail. The instrument 100 may have a distal end 102 configured to perform a surgical action on tissue, and a proximal end 104. The distal end 102 may have a first jaw or anvil 106 and a second jaw or cartridge 108 configured to move toward and away from one another to perform an action on tissue, such as by rotational and/or linear movement. The distal end 102, such as the anvil 106 in particular, may be responsive to a longitudinal movement of an actuator or drive rod 110. In some embodiments, a beam 112, which may be referenced herein as an i-beam, may be configured to move the jaws or anvil 106 and cartridge 108 toward one another in response to an actuator or drive rod 110. The beam 112 may have a tissue clamping, stapling and/or cutting mechanism 126 coupled to a distal end of the beam 112. The beam 112 may have an upper portion 122 and a lower portion 124 be configured to facilitate movement of the clamping, stapling and/or cutting mechanism 126 as the beam 112 moves distally.

In some embodiments, the proximal end 104 may be coupled to or be operatively coupled to the distal end 102 by way of one or more rails 114, 116. For example, the drive rod 110 may be configured to move longitudinally toward the distal end 102.

In some embodiments, one or more bearings 118, 120 may be provided. The bearing(s) 118, 120 may engage the rail(s) 114, 116 and may be movable relative to the rail(s) 114, 116. The bearing(s) 118, 120 may be configured to slide on the rail(s) 114, 116 in response to longitudinal movement of the drive rod 110. The bearing(s) 118, 120 may transfer movement of the rod 110 to the beam 112. In some embodiments, the bearing(s) 118, 120 may be coupled to the beam 112. The bearing(s) 118, 120 may include one or more flange surfaces to engage the beam 112. The bearing(s) 118, 120 may engage one or more flanges in the beam 112, 128

The bearing(s) 118, 120 may have a recess 128 for mounting the bearing(s) 118, 120 onto the rail(s) 114, 116. Those skilled in the art will recognize the bearing(s) 118, 120 may have one or more passages therethrough, and through which the rail(s) 114, 116 may pass as the bearing(s) 118, 120 move longitudinally.

The rail(s) 114, 116 may serve multiple functions. For example, in addition to providing a guide surface for the bearing(s) 118, 120 to transmit forces to the beam 112, the rail(s) 114, 116 may prevent the beam 112 from buckling as the beam 112 is moved longitudinally, and particularly when the beam 112 engages tissue, such as by way of the clamping, stapling and/or cutting mechanism 126. In some embodiments, the rail(s) 114, 116 may be shaped and configured to only contact the beam 112 tangentially. That is, the rail(s) 114, 116 may be curved on the surface adjacent the beam 112, whereby friction between the rail(s) 114, 116 and the beam 112 is minimized. Those skilled in the art will recognize that, for ease of manufacture, the rail(s) 114, 116 may have a circular cross-section as illustrated, though this is not necessarily required.

In some embodiments, the bearing(s) 118, 120 may be slidable relative to the rail(s) 114, 116 and the outer housing or sheath (not shown), whereby the bearing(s) 118, 120 translate a longitudinal force from the drive rod 110 to the distal end 102 of the instrument 100. The bearing(s) 118, 120 may prevent the rail(s) 114, 116 from moving away from the beam 112. The bearing(s) 118, 120 may contact the housing (not shown), the rail(s) 114, 116, and the beam 112 to provide rigidity as the bearing(s) 118, 120 move longitudinally.

Although not illustrated in detail, those skilled in the art will recognize that the anvil 106 may be actuated by the beam 112. For example, the anvil 106 may have a proximal pin feature that rides up or down in a slot (not shown) in the beam 112, as the beam 112 translates forward or back. In some embodiments, the anvil 106 may actuated by a separate anvil actuation member (not shown) or any other means known to those skilled in the art.

The combination of the rails 114, 116 with the sliding bearings 118, 120 allow for multiple stages of support for the beam 112 as it is being displaced. This allows the beam 112 to maintain a low profile as it passes into the distal end 102 of the instrument 100, such as by passing into a slot in a cartridge (not shown.) Embodiments described herein allow for the beam 112 to be fully supported and still leave room for a second, proximal actuator, thereby enabling the instrument 100 to be smaller in such, such as less than 8 millimeters in diameter or less than 5.5 millimeters in diameter.

Figure 5:
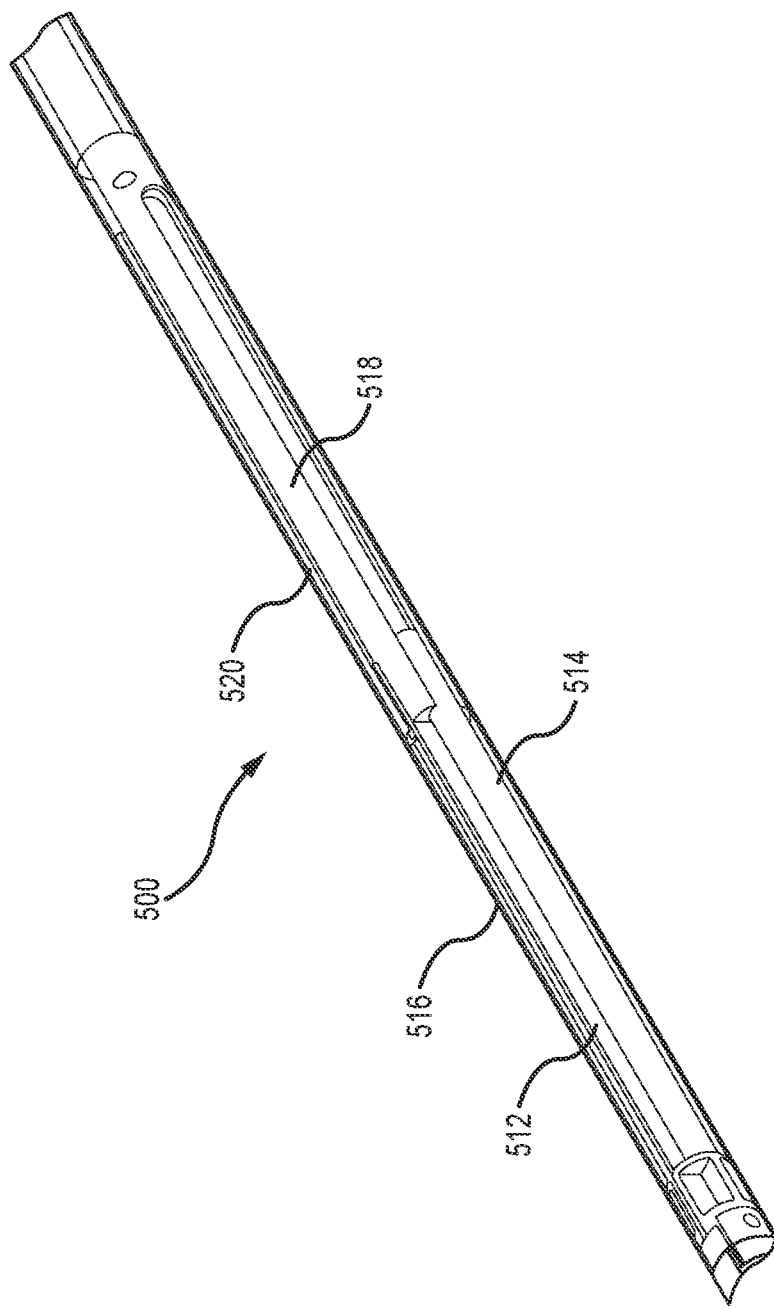
FIG. 5 is a perspective view of some features of an exemplary laparoscopic instrument.

In some embodiments, and as most clearly shown in FIG. 5, an instrument 500 may have rail(s) 514, 516 and bearing(s) 518, 520 substantially as previously described herein. However, in the instrument 500 in FIG. 5, the arrangement of the rail(s) 514, 516 and bearing(s) 518, 520 is such that the bearing(s) 518, 520 support the beam 512 as the bearing(s) 518, 520 move longitudinally.

Figure 6:
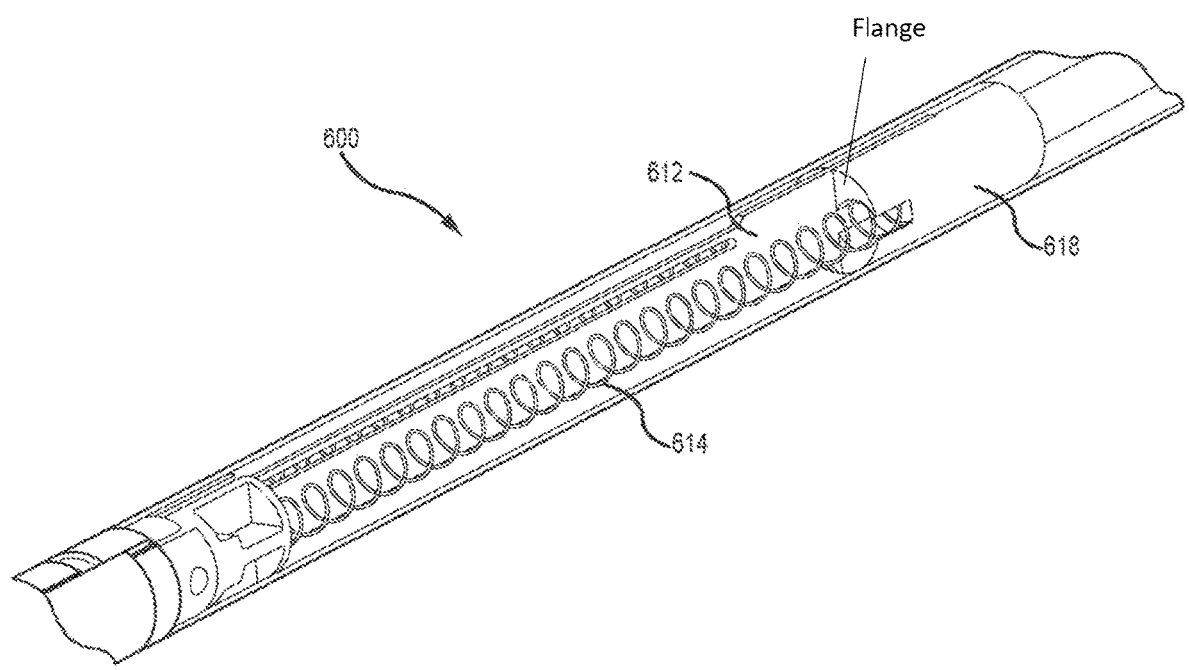
FIG. 6 is a perspective view of some features of an exemplary laparoscopic instrument.

In some embodiments, and as most clearly shown in FIG. 6, an instrument 600 may have one or more springs 614 in lieu of rails, along with one or more bearings 618. The springs 614 may support the beam 612 in much the same manner as previously described herein with reference to the instrument 100.

Each of the various elements disclosed herein may be achieved in a variety of manners. This disclosure should be understood to encompass each such variation, be it a variation of an embodiment of any apparatus embodiment, a method or process embodiment, or even merely a variation of any element of these. Particularly, it should be understood that the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled.

As but one example, it should be understood that all action may be expressed as a means for taking that action or as an element which causes that action. Similarly, each physical element disclosed should be understood to encompass a disclosure of the action which that physical element facilitates. Regarding this last aspect, the disclosure of a "fastener" should be understood to encompass disclosure of the act of "fastening"—whether explicitly discussed or not—and, conversely, were there only disclosure of the act of "fastening", such a disclosure should be understood to encompass disclosure of a "fastening mechanism". Such changes and alternative terms are to be understood to be explicitly included in the description.

Moreover, the claims shall be construed such that a claim that recites "at least one of A, B, or C" shall read on a device that requires "A" only. The claim shall also read on a device that requires "B" only. The claim shall also read on a device that requires "C" only.

Similarly, the claim shall also read on a device that requires "A+B". The claim shall also read on a device that requires "A+B+C", and so forth.

The claims shall also be construed such that any relational language (e.g. perpendicular, straight, parallel, flat, etc.) is understood to include the recitation "within a reasonable manufacturing tolerance at the time the device is manufactured or at the time of the invention, whichever manufacturing tolerance is greater".

Those skilled in the art can readily recognize that numerous variations and substitutions may be made in the invention, its use and its configuration to achieve substantially the same results as achieved by the embodiments described herein.

Accordingly, there is no intention to limit the invention to the disclosed exemplary forms. Many variations, modifications and alternative constructions fall within the scope and spirit of the invention as expressed in the claims.

What is claimed is:

1. An endoscopic surgical instrument, comprising:
a distal end configured to perform an action on tissue;
a drive rod;
a beam movable longitudinally in response to an action on the drive rod;
a rail configured to prevent the beam from buckling as the beam is moved longitudinally; and
a bearing movable relative to at least a part of the rail, wherein at least a part of the bearing is located longitudinally between the drive rod and the beam.

2. The endoscopic surgical instrument of claim 1, wherein the bearing is configured to transmit a longitudinal force from the drive rod to the beam.

3. The endoscopic surgical instrument of claim 1, wherein the distal end comprises a first jaw and a second jaw.

4. The endoscopic surgical instrument of claim 1, wherein the distal end comprises an anvil and a cartridge.

5. The endoscopic surgical instrument of claim 1, wherein the rail provides a guide for the bearing.

6. The endoscopic surgical instrument of claim 1, wherein the bearing is slidable relative to the rail.

7. The endoscopic surgical instrument of claim 1, wherein the bearing is configured to prevent the rail from moving in a direction that is away from the beam as the beam moves longitudinally.

8. The endoscopic surgical instrument of claim 1, wherein the bearing is configured to move longitudinally relative to the rail.

9. The endoscopic surgical instrument of claim 1, wherein the bearing comprises a recess or a passage configured to accommodate a portion of the rail.

10. The endoscopic surgical instrument of claim 1, wherein the bearing comprises a flange configured to engage the beam.

11. The endoscopic surgical instrument of claim 1, wherein the distal end comprises at least one of a clamping mechanism, a stapling mechanism, or a cutting mechanism, and wherein the beam is configured to facilitate movement of the at least one of the clamping mechanism, the stapling mechanism, or the cutting mechanism.

12. The endoscopic surgical instrument of claim 1, wherein at least a part of the rail is distal to the bearing.

13. The endoscopic surgical instrument of claim 1, wherein the distal end of the endoscopic surgical instrument comprises a jaw, and wherein at least a part of the beam is between a proximal end of the jaw and a distal end of the bearing.

14. The endoscopic surgical instrument of claim 1, wherein the bearing is positionally slaved with respect to the beam.

15. The endoscopic surgical instrument of claim 1, wherein the rail comprises an elongate member with a longitudinal axis, at least a longitudinal segment of the elongate member has a cross-sectional shape that is uniform along the longitudinal segment of the elongate member.

16. The endoscopic surgical instrument of claim 1, wherein the rail has a curvilinear surface facing the beam.

17. The endoscopic surgical instrument of claim 1, further comprising another rail, wherein at least a part of the beam is between the rail and the other rail.

18. The endoscopic surgical instrument of claim 1, wherein the bearing is configured to push the beam distally.

19. The endoscopic surgical instrument of claim 1, wherein the bearing comprises an elongate structure having an opening, the opening extending from an exterior surface of the elongate structure, and wherein at least a part of the beam is accommodated in the opening while the beam is in abutment against the bearing.

20. The endoscopic surgical instrument of claim 1, wherein the rail comprises a spring.

21. The endoscopic surgical instrument of claim 1, wherein the bearing is mounted to contact the rail, and is configured to move longitudinally relative to the rail.

22. The endoscopic surgical instrument of claim 1, wherein the rail comprises a guide surface configured to act as a guide for the bearing.

23. An endoscopic surgical instrument, comprising:
   a distal end configured to perform an action on tissue;
   a drive rod;
   a beam movable longitudinally in response to an action on the drive rod;
   a spring configured to prevent the beam from buckling as the beam is moved longitudinally; and
   a bearing;
   wherein at least a part of the bearing is located longitudinally between the drive rod and the beam.

* * * * *